United States Patent [19]

Arai et al.

[11] Patent Number: 4,873,222

[45] Date of Patent: Oct. 10, 1989

[54] PLACENTA-DERIVED ANTICOAGULATING SUBSTANCE

[75] Inventors: Koichi Arai, Urawa; Hideo Yoshizaki, Sayama, both of Japan

[73] Assignee: Kowa Co, Ltd., Nagoya, Japan

[21] Appl. No.: 103,686

[22] Filed: Oct. 2, 1987

[30] Foreign Application Priority Data

Oct. 14, 1986 [JP] Japan .................................. 61-243778

[51] Int. Cl.$^4$ ...................... A61K 37/02; A61K 35/50
[52] U.S. Cl. ........................................... 514/21; 514/2; 424/105
[58] Field of Search ...................... 424/95, 105; 514/2, 514/21

[56] References Cited

U.S. PATENT DOCUMENTS

| | | | |
|---|---|---|---|
| 4,585,654 | 4/1986 | Landaburu et al. | 514/21 |
| 4,638,050 | 3/1987 | Aoki et al. | 424/105 |
| 4,732,891 | 3/1988 | Maki et al. | 424/88 |

FOREIGN PATENT DOCUMENTS

| | | |
|---|---|---|
| 0155852 | 3/1985 | European Pat. Off. . |
| 0217341 | 2/1986 | European Pat. Off. . |

OTHER PUBLICATIONS

Salem et al., "Isolation and Characterization of Thrombomodulin from Human Placenta" *Journal of Bio. Chem.* 259(19), 1984, pp. 12246–12251.

Chem Abstract, vol. 92, No. 11, Mar. 17, 1980, p. 355, Abstract No. 91573c, "Anticoagulant Activity of Peptides from the Human Placenta".

The Journal of Biological Chem., vol. 259, No. 19, Oct. 19, 1984, pp. 12246–12251, "Isolation and Characterization of Thrombomodulin . . . ".

Chem Abstract, vol. 100, No. 11, Mar. 12, 1984, p. 258, Abstract No. 82228a, "Purification and Characterization of Human Placental Proteins . . . ".

Chem Abstract, vol. 101, No. 9, Aug. 27, 1984, p. 428, Abstract No. 70045w, "Comparative Studies on Coagulation and Fibrinolytic Activities . . . ".

Chem Abstract, vol. 102, No. 17, Apr. 29, 1985, p. 389, Abstract No. 146724k, "Preparation of Thrombomodulin from Human Placenta".

Primary Examiner—Johnnie R. Brown
Assistant Examiner—Jean Witz
Attorney, Agent, or Firm—Oblon, Spivak, McClelland, Maier & Neustadt

[57] ABSTRACT

A human placenta-derived anticoagulating substance is prepared by homogenizing a human plancenta, subjecting the resulting homogenate to centrifugal separation, extracting the thus-obtained sediment with a chelating agent, and then separating and purifying the extract. The substance has a molecular weight of 73,000±2,000 as measured in reduced and non-reduced states by SDS-polyacrylamide gel electrophoresis. Its isoelectric point ranges from 6.2 to 6.6 as measured by isoelectric column electrophoresis using an ampholyte. It is inactivated by a heat treatment at 50° C. for 30 minutes, is stable in a pH range of 5.5–8.5 (37° C.) and is also stable in plasma at 37° C. for 15 minutes. It can prolong the recalcification time, prothrombin time and activated partial thromboplastic time.

1 Claim, No Drawings

PLACENTA-DERIVED ANTICOAGULATING SUBSTANCE

BACKGROUND OF THE INVENTION

(1) Field of the Invention

This invention relates to a novel anticoagulating substance and a preparation process thereof.

(2) Description of the Prior Art

The coagulation of blood is considered to start with the development of thromboplastin activity, followed by activation of factors X and V in the blood, further activation of prothrombin into thrombin and final conversion of fibrinogen into fibrin by the action of the thrombin.

For the treatment of diseases ascribed to the coagulation, it is effective to use a substance which is able to impede or deactivate various coagulation factors which take part in the coagulation mechanism, i.e. An anticoagulating substance. Currently known anticoagulating substances include heparin, heparin cofactor-II, antithrombin-III, $\alpha_2$-macroglobulin, $\alpha_1$-trypsin inhibitor, $C_1$-esterase inhibitor, protein C and the like. Recently, Chris P. M. Reutelingsperger, et al. found out, as reported in Eur. J. Biochem., 151, 625–629 (1985), a novel substance having anticoagulating activity and a molecular weight of 32 kDa from umbilical arteries.

However, most of these anticoagulating substances have been confirmed merely to exist and it is only heparin that is now in use as a medicine. Since heparin has a side effect to induce bleeding, strict limitations are however imposed on the manner, amount, etc. of its use. Thus, it is not satisfactory as an anticoagulating agent from the standpoint of safety.

The substance found by Reutelingsperger, et al. is different from the substance of the invention as will be described subsequently. In addition, the activity of the substance has been determined only in the form of a mixture and thus, such a substance is by no means considered to be useful for practical services.

There has hence been a demand for the development of a better anticoagulating agent.

The present inventors previously carried out an extensive investigation with a view toward developing an anticoagulating agent which is safe and is free of side effects. As a results, it was found that a novel anticoagulating substance is obtained from a placenta, which contains a large amount of tissue thromboplastin along with the factor XIII and the fibrinolytic inhibition factor, is considered to have a tendency toward thrombotic formation and is in a special state from the standpoint of the coagulating mechanism, especially, a sediment obtained by centrifuging a human placenta homogenate or a microsome fraction obtained by fractionating the supernatant of the centrifugation. An application for a patent has already been filed based on the finding (U.S. Pat. Application Ser. No. 909,296 filed September 19, 1986).

SUMMARY OF THE INVENTION

The present inventors proceeded with a further investigation with a view toward providing another superior anticoagulating agent and a process for preparing same. As a result, it was also found that an additional substance having similar anticoagulating activity is contained in fractions different from those containing the above substance. It has now been succeeded in isolating the additional substance, leading to completion of this invention.

In one aspect of this invention, there is thus provided a human placenta-derived anticoagulating substance having the following properties:

(1) molecular weight (SDS-polyacrylamide gel electrophoresis, reduced and non-reduced states): 73,000±2,000;

(2) isoelectric point (isoelectric column electrophoresis using an ampholyte): 6.2–6.6;

(3) stability:
  (a) inactivated by a heat treatment at 50° C. for 30 minutes,
  (b) stable in a pH range of 5.5–8.5 (37° C.),
  (c) stable in plasma at 37° C. for 15 minutes; and (4) effects:
  (a) capable of prolonging the recalcification time,
  (b) capable of prolonging the prothrombin time,
  (c) capable of prolonging the activated partial thromboplastin time.

In another aspect of this invention, there is also provided a process for preparing the above human placenta-derived anticoagulating substance, which process comprises homogenizing a human placenta, subjecting the resulting homogenate to centrifugal separation, extracting the thus-obtained sediment with a chelating agent, and then separating and purifying the extract.

The anticoagulating substance of the invention (which may hereinafter be referred to as "the invention substance") has strong anticoagulating activity and exhibits still stronger activity, in particular, where the tissue thromboplastin activity has been exacerbated, namely in an exacerbated coagulation state. Hence, an anticoagulant containing the invention substance as an effective component has less side effects and is thus harmless.

The above and other objects, features and advantages of the present invention will become apparent to one of ordinary skill in the art from the following description of the invention and the appended claims.

DETAILED DESCRIPTION OF THE INVENTION AND PREFERRED EMBODIMENTS

The invention substance can be prepared, for example, as follows.

A placenta homogenate is first prepared from the human precenta and then separated centrifugally. The homogenization is effected in the following manner. After cutting off the amnion and the like from the placenta, the placenta is washed thoroughly with a physiological saline, followed by homogenization by the use of a Waring blender and Polytron. The resulting homogenate is subjected to centrifugal separation to obtain a supernatant and a sediment.

The thus-obtained sediment of the placenta homogenate is washed thoroughly with a buffer and is centrifuged again. A sediment thus washed is collected, followed by its extraction. Namely, the washed sediment is immersed in a buffer, which contains a chelating agent such as EDTA, EGTA, oxalic acid, citric acid, sodium nitrilotriacetate or phosphoric acid, and is allowed to stand overnight at 4° C.–8° C. Thereafter, the mixture is centrifuged to collect a supernatant as an extract. Here, the extraction may be carried out in the presence of a surfactant such as Triton X-100 (trade name), Lubrol (trade mark), SDS, deoxycholic acid or the like.

The supernatant is further fractionated by ultracentrifugal separation at 50,000 to 100,000×g to obtain a microsome fraction as a sediment. An extract containing the substance of this invention can also be obtained from the microsome fraction in the same manner as described above, namely, by extracting the microsome fraction with a chelating agent and/or a surfactant and then subjecting the resultant extract to ultracentrifugal separation to collect a supernatant.

The thus-obtained extract is subjected to ammonium sulfate fractionation. The ammonium sulfate fractionation is effected by a two-step procedure. First, solid ammonium sulfate is added to 35% of its saturated concentration to the extract, followed by centrifugation to collect a supernatant. Ammonium sulfate is then added to the supernatant until its concentration reached 85% of its saturated concentration, followed by centrifugation to collect a sediment.

The resulting ammonium sulfate fraction is then purified by known isolation and purification procedures including, for example, dialysis, ion exchange chromatography, gel filtration, adsorption chromatography, hydrophobic chromatography, isoelectric point column electrophoresis, affinity chromatography using lectin or an antibody, and the like either singly or in combination, thereby obtaining the invention substance. For example, a fraction obtained by subjecting the chelating agent extract to ammonium sulfate fractionation is dialyzed thoroughly. When the resulting dialyzate is eluted in accordance with the linear concentration gradient method in which DEAE-Toyopearl (trade mark) was used, an active fraction is eluted immediately after the elution of albumin. After the active fraction is dialyzed, it is concentrated and then subjected to gel filtration through Sephadex G-100 (trade name) or affinity chromatography on a column of collagen, elastin, gelatin, actin or the like, thereby to obtain the invention substance.

The thus-obtained invention substance has such properties as described above, and their measurement method and results will next be described more specifically.

(1) Measurement of molecular weight

As a result of a measurement by SDS-polyacylamide gel electrophoresis (10% polyacrylamide gel; reduced and non-reduced state), the molecular weight was found to be 73,000±2,000.

(2) Measurement of isoelectric point

According to a measurement by isoelectric point column electrophoresis using ampholyte (pH 3.5–10, 4° C.) at 300 V for 48 hours, the isoelectric point was found to be 6.2–6.6.

The measurement was conducted by providing an electrofocusing column ("LKB 8100-1", trade name; 110 ml), establishing an anode at the top of the column, preparing a density gradient using sucrose containing the Ampholine carrier ampholyte solution (pH 3.5–10.0) at a final concentration of 0.83%. And then, 1.3 mg of substance of this invention layered in the middle of the density gradient was subjected to electrophoresis at 300 V for 48 hours (4° C.). After the electrofocusing was completed, fractions of 1 ml were collected. Fractions were measured with respect to pH value and prothrombin time prolonging effects, followed by SDS polyacrylamide gel electrophoresis. The substance of the invention was observed in the fractions within a pH range of 6.2–6.6. With a view toward confirming whether the occurrence of the insoluble matter did not affect the measurement of the isoelectric point, electrophoresis was conducted further for 14 hours and 62 hours respectively under the above-mentioned conditions by using a pH gradient which contained "Triton X-100" (trade name) to give a final concentration of 0.1%, whereby its isoelectric point was measured. An insoluble matter was formed in each of the 14-hour and 62-hour electrophoresis. The insoluble matter however disappeared after eluted from a column. The substance of this invention showed prothrombin time prolonging effects and were detected by SDS-polyacrylamide gel electrophoresis in a pH range of 6.2–6.6. In the 62-hour electrophoresis, the substance of this invention was observed not only in the pH range of 6.2–6.6 but also in a pH range of 5.4–5.8. However, the prothrombin time prolonging effects measured in the pH range of 5.4–5.8 were weaker than those measured in the pH range of 6.2–6.6.

(3) Stability tests (a) Stability to heat treatment

The invention substance was treated at different temperatures (0–80° C.) for 30 minutes each and the anticoagulating activity was measured in accordance with the prothrombin time method. As a result, it was found that the activity was completely lost at temperatures of 50° C. and higher.

(b) pH stability

Various buffers of pH 3.5–pH 10.0 were separately added, followed by a treatment at 4° C. or 37° C. for 18 hours. Thereafter, the remaining anticoagulating activity was measured by the prothrombin time method. As a result, no reduction of the activity was observed over a pH range of 5.5–10.0 at 4° C. and over a pH range of 5.5–8.5 at 37° C.

(c) Stability in plasma:

The invention substance was added to plasma and incubated at 37° C. for 15 minutes, followed by a measurement of the remaining anticoagulating activity by the recalcification time method. As a result, no activity reduction was observed.

(4) Effects (a) Effects to the recalcification time

Standard plasma (100 μl, product of Ortho Diagnostic Systems Inc.) and 100 μl of a solution of the invention substance were mixed. Three minutes later, 100 μl of a 0.025 M calcium chloride solution was added and the coagulation time was measured. As a result, strong prolonging effects to the recalcification time were recognized as shown in Table 1.

TABLE 1

| Amount of the invention substance added (μg) | 0 | 0.3 | 1.0 | 3.0 |
|---|---|---|---|---|
| Coagulation time (sec) | 246 | 279 | 639 | >3600 |

(b) Effects to the prothrombin time (PT)

Mixed were 100 μl of a PT reagent (Lyoplastin, product of Mochida Pharmaceutical Co., Ltd.), which had been diluted with a 20 mM solution of calcium chloride, and 100 μl of a solution of the invention substance. Three minutes later, 100 μl of standard plasma was added and coagulation time was measured. As a result, strong PT-prolonging effects were recognized as shown in Table 2.

TABLE 2

| Amount of tissue thromboplastin (mg) | 0.1 | 0.1 | 0.1 | 0.1 |
|---|---|---|---|---|
| Amount of the invention substance added (μg) | 0 | 2 | 5 | 10 |
| Coagulation time (sec) | 18 | 28 | 110 | 208 |

(c) Effects to the activated partial thromboplastin time (APTT)

Ten microliters of an APTT reagent (activated thrombophax, product of Ortho Diagnostic Systems Inc.) and 90 μl of a solution of the invention substance were mixed. Two minutes later, 100 μl of standard plasma was added. Six minutes later, 100 μl of a 0.025 M calcium chloride solution was added to determine the coagulation time. As a result, strong APTT prolonging effects were recognized as shown in Table 3.

TABLE 3

| APTT reagent (μl) | 10 | 10 | 10 | 10 |
|---|---|---|---|---|
| Amount of the invention substance added (μg) | 0 | 2.5 | 5 | 20 |
| Coagulation time (sec) | 78 | 102 | 251 | 2267 |

(5) Amino acid composition

Portions of the invention substance were hydrolyzed with 5.7 N hydrochloric acid at 110° C. for 24, 48 and 72 hours separately, followed by measurement by a Beckmann Amino Acid Analyzer Model 6300E (trade name). Results are shown in Table 4.

TABLE 4

| Amino acid | Analysis data (mol %) |
|---|---|
| Aspartic acid | 11.0 |
| Threonine | 6.1 * |
| Serine | 5.8 * |
| Glutamic acid | 12.7 |
| Proline | 2.4 |
| Glycine | 7.0 |
| Alanine | 8.9 |
| ½Cystine | 0.5 |
| Valine | 3.7 ** |
| Methionine | 2.8 |
| Isoleucine | 6.2 ** |
| Leucine | 10.0 |
| Tyrosine | 3.4 |
| Phenylalanine | 3.8 |
| Histidine | 1.9 |
| Lysine | 7.6 |
| Arginine | 6.3 |
| Total | 100.0 |

In Table 4, the unasterisked analysis data are those obtained after the 24-hour hydrolysis. The single-asterisked analysis data are those obtained by extrapolation to 0 hour. The double-asterisked analysis data are those obtained after the 72-hour hydrolysis.

The article of Reutelingsperger, et al. referred to above discloses merely the molecular weight of their substance as measured by SDS-PAGE along with their finding that their substance was a protein which was inactivated by a heat treatment at 56° C. Reutelingsperger, et al. had not isolated and identified their substance. Although it is therefore not quite certain, the invention substance obtained in the manner described above is believed to be different from the substance of the prior art publication because the substance of the prior art publication was extracted with a tris-HCl buffer from the umbilical cord and its isoelectric point and molecular weight are different from those of the invention substance.

As a preparation form of the invention substance upon its use as an effective component in an anticoagulant, an injection may be mentioned. The injection may preferably be in the form of lyophilized powder, which is administered by dissolving same in distilled water for injection, physiological saline, or the like before use. The suitable administration route is intravenous.

The preferable dose may generally be in a range of from 10 μg to 10 mg/kg·day, although it varies depending on the severity of each disease, the body weight of each patient, etc. It should be noted that the invention substance develops no abnormality on use within the above dose range and is thus harmless. For the formulation of the invention substance into an injection, albumin, gelatin, mannitol or the like may be added as a stabilizer by way of example. The addition of such a stabilizer can avoid the deactivation of the invention substance which would otherwise occur due to its decomposition, adsorption and the like during its formulation process, and can also improve the storage stability of the preparation.

EXAMPLES

The present invention will hereinafter be described by the following Examples.

EXAMPLE 1

(i) Five human placentae (about 2,500 g) were minces subsequent to removal of membranes and the like and thorough washing with a physiological saline. Two liters of a 50 mM tris-hydrochloric acid buffer (pH 7.4) were then added, followed by grinding in a Waring blender and by further comminution in Polytron. The resulting homogenate was subjected to centrifugal separation at 7,000 r.p.m. for 15 minutes to collect a sediment. Two liters of a 50 mM tris-hydrochloric acid buffer (pH 7.4) were added again to the thus-collected sediment, and the resulting mixture was homogenized in Polytron and then subjected to centrifugal separation at 7,000 r.p.m. for 15 minutes to obtain a washed sediment. The above procedure was repeated several times until blood components were removed to obtain about 930 g of a washed sediment finally.

(ii) About 2 liters of a 50 mM tris-hydrochloric acid buffer containing 50 mM of EDTA were added to 900 g of the sediment obtained in the above procedure (i), followed by homogenization in the Waring blender The resulting homogenate was agitated overnight at 4° C., followed by centrifugal separation at 7,000 r.p.m. for 15 minutes to obtain 2 liters of an extract.

(iii) Solid ammonium sulfate was added to the extract obtained in the above (ii) to 35% of its saturated concentration. After allowing the resultant mixture to stand at 4° C. for 30 minutes to several hours, it was centrifuged at 7,000 r.p.m. for 15 minutes to collect a supernatant. Ammonium sulfate was added further to the supernatant to 85% of its saturated concentration. The resultant mixture was allowed to stand at 4° C. for 2 hours, followed by centrifugation at 7,000 r.p.m. for 15 minutes to collect a sediment. The thus-obtained sediment was dissolved in a small amount of a 20 mM tris-hydrochloric acid buffer and thoroughly dialyzed overnight at 4° C. against the same buffer. The precipitate formed during the dialysis was removed by centrifugation at 7,000 r.p.m. for 15 minutes to obtain 390 ml of a dialyzate.

(iv) The thus-obtained dialyzate was adsorbed on DEAE-Toyopearl (trade name; φ5.5×1.9 cm) which had been equilibrated with a 20 mM tris-hydrochloric acid buffer (pH 7.4) and washed thoroughly with the same buffer. Using 4-liter portions of the same buffer which portions contained 0 to 0.3 M of sodium chloride respectively, elution was then performed at a rate of 20 ml per fraction in accordance with the linear concentration gradient method. Active fractions were eluted around a sodium chloride concentration of approximately 0.2 M, thereby obtaining 200 ml of active fractions.

(v) The thus-obtained active fractions were centrifuged using a Diaflow Membrane Filter YM-10 (trade name).

The concentrate was subjected to gel filtration using Sephadex G-100 (trade name; φ4.5×75 cm) and eluted at a rate of 8 ml per fraction with a physiological saline. Active fractions 70–82 were collected and concentrated by ultrafiltration to obtain 14 ml of the invention substance (protein weight: 59.3 mg, Lowry method).

EXAMPLE 2:

Five human placentae were treated in accordance with the procedure of Example 1, thereby obtaining about 200 ml of active fractions eluted around a sodium chloride concentration of 0.2 M from DEAE-Toyopearl (trade name).

After dialyzing the active fractions overnight against a 50 mM tris-hydrochloric acid buffer (pH 7.4) which contained 5 mM of calcium chloride, a 100 ml portion of the dialyzate was adsorbed on a collagen column (product of Sigma Corporation; Type I derived from Achilles tendons; 5 g, 2.5×8 cm) which had been equilibrated beforehand with the same buffer. After washing the column thoroughly with the same buffer until the absorption of $A_{280}$ became 0.05 or lower, the column was eluted at a rate of 5 ml per fraction with a 50 mM tris-hydrochloric acid buffer containing 10 mM of EDTA. Protein peaks were collected to obtain 40 ml of the invention substance (protein weight: 15 mg).

EXAMPLE 3

Adsorbed on an elastin column (product of NBC Company; 0.5 g, 1.3×1 cm) was 10 ml of a sample of Example 2 which had been dialyzed against a 50 mM tris-hydrochloric acid buffer containing 5 mM of calcium chloride. The eluilibration, washing and elution of the column were conducted in the same manner as in Example 2, thereby obtaining 15 ml of the invention substance (protein weight: 2 mg).

We claim:

1. A human placenta-derived anticoagulating substance having the following properties:
   (1) molecular weight (SDS-polyacrylamide gel electrophoresis, reduced and non-reduced states): 73,000±2,000;
   (2) isoelectric point (isoelectric column electrophoresis using an ampholyte): 6.2–6.6;
   (3) stability:
      (a) inactivated by a heat treatment at 50° C. for 30 minutes,
      (b) stable in a pH range of 5.5–8.5 (37° C.),
      (c) stable in plasma at 37° C. for 15 minutes;
   (4) effects:
      (a) capable of prolonging the recalcification time,
      (b) capable to prolonging the prothrombin iime,
      (c) capable of prolonging the activated partial thromboplastin time; and
   (5) amino acid composition as determined by hydrolysis with 5.7 N HCl at 110° C.:

| Amino acid | Analysis data (mol %) |
| --- | --- |
| Aspartic acid | 11.0 |
| Threonine | 6.1* |
| Serine | 5.8* |
| Glutamic acid | 12.7 |
| Proline | 2.4 |
| Glycine | 7.0 |
| Alanine | 8.9 |
| ½ Cystine | 0.5 |
| Valine | 3.7** |
| Methionine | 2.8 |
| Isoleucine | 6.2** |
| Leucine | 10.0 |
| Tyrosine | 3.4 |
| Phenylalanine | 3.8 |
| Histidine | 1.9 |
| Lysine | 7.6 |
| Arginine | 6.3 |
| Total | 100.0 | in which the unasterisked analysis data are those obtained after the 24-hour hydrolysis, the single-asterisked analysis data are those obtained by extrapolation to 0 hour, and the double-asterisked analysis data are those obtained after the 72-hour hydrolysis.

* * * * *